(12) United States Patent
Schibli et al.

(10) Patent No.: US 11,590,317 B2
(45) Date of Patent: Feb. 28, 2023

(54) CATHETER SYSTEM

(71) Applicants: Heraeus Deutschland GmbH & Co. KG, Hanau (DE); Heraeus Medical Components LLC, St. Paul, MN (US)

(72) Inventors: Stefan Schibli, Rodenbach (DE); Michael Grimm, Bad Vilbel (DE); Ronald Von Wald, Centerville, MN (US); Mark A. Hjelle, Fridley, MN (US); Ilias Nikolaidis, Frankfurt am Main (DE); Malte Naujoks, Darmstadt (DE)

(73) Assignees: Heraeus Deutschland GmbH & Co. KG, Hanau (DE); Heraeus Medical Components LLC, St. Paul, MN (US)

( * ) Notice: Subject to any disclaimer, the term of this patent is extended or adjusted under 35 U.S.C. 154(b) by 441 days.

(21) Appl. No.: 16/151,843

(22) Filed: Oct. 4, 2018

(65) Prior Publication Data

US 2019/0105466 A1  Apr. 11, 2019

(30) Foreign Application Priority Data

Oct. 5, 2017  (EP) .................................. 17194869

(51) Int. Cl.
| | |
|---|---|
| *A61M 25/01* | (2006.01) |
| *A61B 18/14* | (2006.01) |
| *A61M 25/00* | (2006.01) |
| *A61B 34/00* | (2016.01) |
| *A61N 1/36* | (2006.01) |
| *A61B 5/0215* | (2006.01) |

(Continued)

(52) U.S. Cl.
CPC ..... *A61M 25/0105* (2013.01); *A61B 18/1492* (2013.01); *A61B 34/76* (2016.02); *A61M 25/0012* (2013.01); *A61B 5/0215* (2013.01); *A61B 2018/00351* (2013.01); *A61B 2018/00375* (2013.01); *A61B 2018/00511* (2013.01); *A61B 2018/00577* (2013.01); *A61B 2018/1407* (2013.01); *A61B 2018/1467* (2013.01); *A61B 2090/065* (2016.02);

(Continued)

(58) Field of Classification Search
None
See application file for complete search history.

(56) References Cited

U.S. PATENT DOCUMENTS

| | | | | |
|---|---|---|---|---|
| 2003/0236445 | A1* | 12/2003 | Couvillon, Jr. ........ | A61B 5/062 600/114 |
| 2005/0014995 | A1* | 1/2005 | Amundson ............ | A61B 90/36 600/105 |

(Continued)

FOREIGN PATENT DOCUMENTS

| | | |
|---|---|---|
| EP | 3178428 | 6/2017 |
| EP | 3178430 | 6/2017 |

*Primary Examiner* — Alex M Valvis
*Assistant Examiner* — Aurelie H Tu
(74) *Attorney, Agent, or Firm* — Dicke, Billig & Czaja, PLLC

(57) ABSTRACT

One aspect relates to a catheter system, a use of such catheter system and a manufacturing method for such catheter system. The catheter system includes an at least partially flexible catheter body, at least a ring electrode, and at least a strain gauge. The ring electrode surrounds at least a portion of the flexible catheter body. The strain gauge is allocated to the ring electrode and the strain gauge is configured to measure a deformation of the flexible catheter body at a position allocated to the ring electrode to detect a contact between the ring electrode and tissue.

19 Claims, 10 Drawing Sheets

(51) Int. Cl.
  *A61B 18/00* (2006.01)
  *A61N 1/362* (2006.01)
  *A61M 25/10* (2013.01)
  *A61F 2/95* (2013.01)
  *A61B 90/00* (2016.01)
(52) U.S. Cl.
  CPC ......... *A61B 2562/0261* (2013.01); *A61F 2/95* (2013.01); *A61M 25/0068* (2013.01); *A61M 25/10* (2013.01); *A61M 2025/0166* (2013.01); *A61N 1/362* (2013.01); *A61N 1/3605* (2013.01); *A61N 1/36039* (2017.08)

(56) References Cited

U.S. PATENT DOCUMENTS

| | | | |
|---|---|---|---|
| 2005/0080429 A1* | 4/2005 | Freyman | A61B 5/061 600/117 |
| 2006/0181525 A1* | 8/2006 | Larsen | G06F 3/03545 345/179 |
| 2006/0241366 A1* | 10/2006 | Falwell | A61B 5/287 600/374 |
| 2007/0048521 A1* | 3/2007 | Istvan | D01F 9/20 428/367 |
| 2010/0069733 A1* | 3/2010 | Kastelein | A61B 5/6857 600/374 |
| 2011/0160556 A1 | 6/2011 | Govari | |
| 2012/0265271 A1* | 10/2012 | Goetz | A61N 1/36128 607/59 |
| 2012/0312102 A1* | 12/2012 | Alvarez | F16J 15/3296 73/862.041 |
| 2016/0096964 A1* | 4/2016 | Fukuyo | C09D 7/62 252/511 |
| 2017/0203096 A1 | 7/2017 | Schibli et al. | |
| 2017/0221646 A1* | 8/2017 | Lee | B29C 67/04 |
| 2017/0241036 A1* | 8/2017 | Romann | H01G 4/33 |
| 2018/0029891 A1* | 2/2018 | Tonegawa | H01M 4/661 |

\* cited by examiner

CATHETER SYSTEM

CROSS-REFERENCE TO RELATED APPLICATION

This Utility Patent Application claims priority to Application No. EP 17194869.8, filed on Oct. 5, 2017 which is incorporated herein by reference.

BACKGROUND

One aspect relates to a catheter system, a use of such catheter system and a manufacturing method for such catheter system. In the invasive medical field, there is a need for improved catheter systems and for example, for catheter system, which allow a better control. The efforts in minimal invasive procedures and robotic surgery push this trend and generate more and more need to have, for example, a haptic feedback incorporated into catheter systems and other medical devices.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
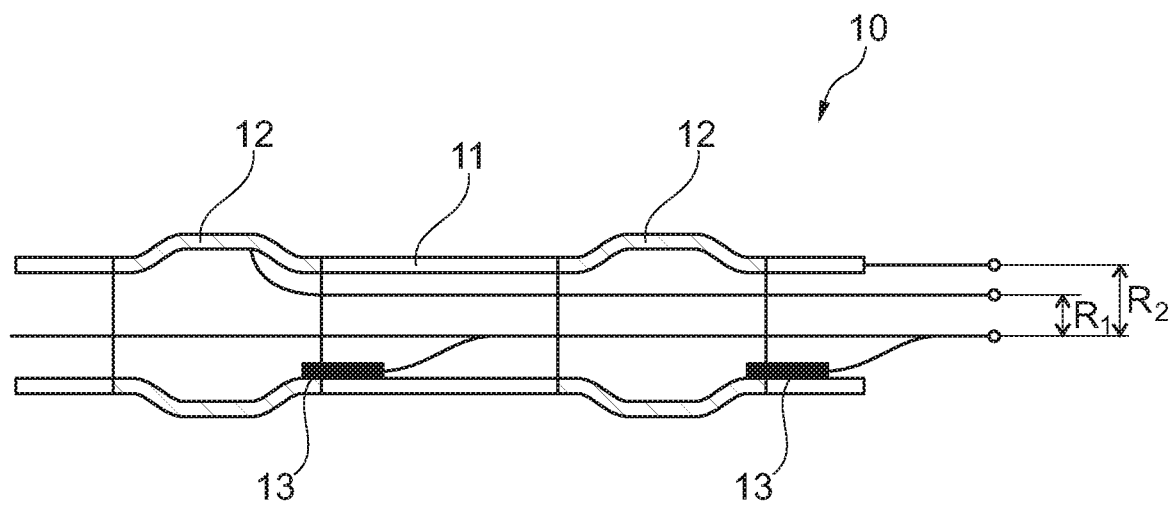
FIG. 1 illustrates a schematic drawing of an example of a catheter system according to one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

There may be a need to provide an improved catheter system that allows a superior control of a catheter system.

At least some problems are solved by the subject-matters of the independent claims, wherein further embodiments are incorporated in the dependent claims. It should be noted that the aspects of one embodiment described in the following apply also to the catheter system, the use of such catheter system and the manufacturing method for such catheter system.

According to one embodiment, a catheter system is presented. The catheter system includes an at least partially flexible catheter body, at least a ring electrode, and at least a strain gauge.

The ring electrode surrounds at least a portion of the flexible catheter body.

The strain gauge is allocated to the ring electrode. The strain gauge is configured to measure a deformation of the flexible catheter body at a position allocated to the ring electrode to detect a contact between the ring electrode and tissue.

The catheter body may be a plastic tube. The ring electrode may be a ring shaped or annular electrode. It may fully surround the catheter body or extend only along a part of the catheter body, in one embodiment along a major part of the catheter body. The strain gauge may be a device suitable to measure strain on an object based on a deformation of the object. The deformation of the catheter body may be a deflection. The contact between the ring electrode and tissue may be a physical contact, in one embodiment a point contact. The term "allocated" may be understood in that a strain gauge is assigned to a ring electrode. The allocation or assignment may be meant electrically, logically and/or spatial. The strain gauge may have an electrical, logical and/or spatial connection to the ring electrode. In an example, the strain gauge is arranged in the proximity of the ring electrode. In case of several strain gauges and several ring electrodes, a 1:1 attribution of strain gauges and ring electrodes can be provided, which means that each ring electrode is provided with a corresponding strain gauge.

The use of a flexible catheter body allows a movement of the catheter system in an for example, human body and a measurement of the catheter body's deformation at the position of the strain gauge and thereby at the position of the ring electrode. The measured deformation or deflection can be used to detect a contact between the strain gauge and thereby the ring electrode and surrounding tissue and to calculate a contact force of the strain gauge and thereby the ring electrode when using the ring electrode for, for example, pulmonary vein ablation. This means, a contact or a contact force is not directly measured, but indirectly by means of a measurement of the deformation of the flexible catheter body caused by contact or contact pressure.

The catheter system according to one embodiment thereby provides at least one of the following advantages: enabling a superior control of the catheter system to ensure proper therapy, avoiding a damage of surrounding tissue, providing a possibility to form very small devices, high flexibility of the device, superior sensitivity, easy and cheap manufacture, flexibility to be manufactured in all kinds of shapes and sizes, flexibility to be manufactured with particular elastic modulus or other physical properties, etc.

The catheter system according to one embodiment can be used for example, as force sensor and, for example, as contact force sensor or clamping force sensor for catheters, guidewires, surgery tools or leads. It may also be used for any kind of smart and flexible devices, as for example, smart textiles or touch panels, to give haptic feedback.

In an example, the strain gauge is configured to output a change of electrical resistance depending on the deformation of the flexible catheter body at the position allocated to the ring electrode. The catheter system may further include a processing unit configured to calculate a contact force between the ring electrode and tissue based on the change of electrical resistance. The processing element may be configured to process an electrical resistance detected by the strain gauge into a value of compressive load applied to the catheter system. In more detail, the processing element may be configured to process a decrease of electrical resistance detected by the strain gauge into a value of compressive load applied to the catheter system. The processing element may be an analog digital converter.

In an example, the processing unit is spaced apart from the ring electrode. This provides the advantage that the generally heat sensitive processing unit or sensor can be placed at a distance to the actual procedure where for example, ablation and therefore heat occurs, which would otherwise negatively affect the processing unit.

In an example for pulmonary vein ablation (also called pulmonary vein antrum isolation or PVAI) to treat atrial fibrillation (an abnormal heart rhythm), the catheter body may form a helical shape to surround an area of tissue. The catheter system may include several strain gauges and several ring electrodes. They might be distributed along at least a part of the catheter body. The strain gauge may be a strain gauge body with a tubular shape extending at least partially inside the catheter body. The tubular strain gauge body may include several strain gauges arranged with distances between each other. The catheter system may include at least a first and a second strain gauge and at least a first and a second ring electrode. The first strain gauge may be allocated to the first ring electrode and the second strain gauge may be allocated to the second ring electrode. The strain gauges may be configured to measure a deformation of the flexible catheter body at a first and a second position allocated to the first and the second ring electrode to detect a contact between the first ring electrode and the tissue and/or the second ring electrode and the tissue. In this example, the catheter body is a so-called Pig Tail catheter. The Pig Tail catheter has a shape of a pig tail, which means it is curled or has loops.

The benefit of this embodiment is to make for example, a pulmonary vein ablation procedure faster, because the pulmonary vein junction can be simultaneously ablated all around. Another benefit of this embodiment is to make the pulmonary vein ablation procedure more reliable. According to the prior art, if one spot is not well ablated, the patient will need to be re-hospitalized to repeat the procedure. Further, it is very difficult to know if the ablation procedure was successful or not. Another benefit is that this embodiment has less hysteresis than using conventional punctual contact force detection, which is important as medical procedures take place in constant moving environments (beating heart, breathing . . . ) and the measured forces change fast.

In another example, the ring electrode and the strain gauge are arranged at a distal tip of the catheter body and the ring electrode is dome-shaped. This embodiment provides a perfect control of an initial contact of the catheter system and the surrounding tissue, for example, a heart wall.

In an example, the strain gauge is made of a piezoresistive material including a carbon component and an elastomer component. It may provide the benefit to be elastic enough to not limit a flexibility of the catheter system and to give a very sensitive feedback of a change of electrical resistance. In more detail:

In an example, the carbon component includes carbon particles. The carbon particles may be so-called Porocarb® material made by Heraeus. It will be explained further below in more detail.

The carbon particles may include macropores. The term "macropore" may be understood as a pore with a size between 50 and 1000 nm. The macropore size may be measured by Hg porosimetry and for example, based the ISO 15901-1 (2005) standard.

In an example, the elastomer component includes polymeric chains.

In an example, at least some of the macropores in the carbon particles may be infiltrated by the polymeric chains to form a piezoresistive interconnection between the carbon particles. This means the macropores in the carbon particles may be interconnected by the infiltration of polymeric chains of the elastomer component into the macropores. As a result, the piezoresistive interconnection between the carbon particles may be implemented by the polymeric chains, which may be configured to rearrange when the piezoresistive material is subjected to a compressive load so that electrical paths form between the carbon particles to decrease an electrical resistance of the piezoresistive material.

The term "piezoresistive" may be understood in that the piezoresistive material is subjected to a change of its electrical resistivity when mechanical stress is applied to the piezoresistive material. The mechanical stress may be an elastic, isostatic or unidirectional compressive load. The mechanical stress may be at least one of a group including force, pressure, motion, vibration, acceleration and elongation.

The term "piezoresistive interconnection" may be understood in that the carbon component and the elastomer component are interconnected to form a compound material, which has a piezoresistive effect. This means, when mechanical stress is applied to the compound of carbon component and elastomer component, the compound illustrates a change of its electrical resistivity and for example, a decrease of its electrical resistivity and an increase of electrical conductivity.

The term "piezoresistive material" may be understood as a material including elastomer filled with porous carbon particles to form part of a resistive sensor, which illustrates a negative change of electrical resistance when subjected to pressure.

The term "elastomer component" may be understood as a component including an elastomer, which is an elastic polymer. The molecular structure of elastomers can be imagined as a 'spaghetti and meatball' structure, with the meatballs signifying cross-links. Elasticity is derived from an ability of long chains to reconfigure themselves to distribute an applied stress. Covalent cross-linkages ensure that the elastomer will return to its original configuration when the mechanical stress is removed.

The term "polymeric chains" may be understood as covalently bonded links between monomers forming a network. The polymeric chains may block an electric conductivity between the carbon particles in an unloaded condition of the piezoresistive material. When a load, as for example, mechanical pressure, is applied to the piezoresistive material, the polymeric chains may be compressed and the electrically conductive carbon particles may contact each other to implement an electric conductivity of the piezoresistive material.

The term "infiltrated" may be understood in that polymeric chains penetrate into pores of the carbon particles. The polymeric chains may also penetrate through pores of carbon particles and thereby link several carbon particles to each other.

As a result, the piezoresistance of the interconnection may be based on the fact that the polymeric chains between the carbon particles rearrange and relax when the piezoresistive material is subjected to a compressive load. The rearrangement and relaxation enables a formation of electrical paths between the electrically conductive carbon particles and consequently reduces the electrical resistance of the piezoresistive material.

The herein described materials of the catheter system according to one embodiment may provide at least one of the following advantages: a possibility to form piezoresistive devices illustrating a superior sensitivity, a possibility to form very small piezoresistive devices, a possibility to form flexible piezoresistive devices, and a possibility to form a piezoresistive device with a large measuring or detection range, a small dependence on temperatures and/or a very good relaxation behavior. Further, the materials of the catheter system according to one embodiment may allow an easy and cheap manufacture, may be manufactured in all kinds of shapes and sizes (for example, by 3D and conventional printing, drawing, molding, injection molding, painting, spraying, screen printing, coating etc.) and may be adapted during manufacture in view of its elastic modulus, flexibility etc. by for example, tuning the physical properties of the elastomer component.

The dimensions of the macropores of the carbon particles may be adapted to the dimensions of polymeric precursors of the elastomer component. This means, the diameter of a polymer emulsion particle may be in a range of a diameter of a macropore. The interconnection between the carbon particles may further include that at least some of the carbon particles are linked by the polymeric chains of the elastomer component. Such rigid mechanical interconnection between carbon particles and polymeric chains enables a most complete geometrical restoring after elastic compression of the material.

In an example, the carbon particles are highly porous. The term "highly porous" may be understood in that the carbon particles may have a total pore volume between 0.7 and 3.5 cm$^3$/g, and in one embodiment between 0.9 and 2.5 cm$^3$/g. The pore volume may be measured by Hg porosimetry and for example, based on the ISO 15901-1 (2005) standard.

In an example, the macropores in the carbon particles have a macropore volume between 0.6 and 2.4 cm$^3$/g, and in one embodiment between 0.8 and 2.2 cm$^{-3}$/g. The macropore volume may be measured by Hg porosimetry and for example, based on the ISO 15901-1 (2005) standard. The large macropore volume enables a filling by the polymeric chains of the elastomer component and thus a fixation of the polymeric chains.

In an example, the carbon particles further include mesopores with a size between 2 and 50 nm and a mesopore volume between 0.05 and 0.2 cm$^3$/g, and in one embodiment between 0.1 and 0.15 cm$^3$/g. The mesopore size and/or the mesopore volume may be measured by Hg porosimetry and for example, based on the ISO 15901-1 (2005) standard.

In an example, the carbon particles include no micropores with a size smaller 2 nm, which may be understood as having a micropore volume of less than 0.01 cm$^3$/g. The micropore size and/or the micropore volume may be measured by measured by physical gas adsorption according to BET (Brunauer-Emmett-Teller) and for example, based on DIN ISO 9277:1995.

In an example, the carbon component is graphitized. It may be graphitized to a graphitization degree between 60 and 80%, and in one embodiment to a graphitization degree of over 70%. The term "graphitized" may be understood in that a formation of graphitic carbon is initiated by an exposure to elevated temperatures between for example, 1400 to 3000° C. During graphitization, micropores tend to disappear, mesopores rearrange and macropores remain constant. The result is a graphitized, porous carbon component including carbon particles with a large amount of macropores. The macropores can be linked with each other. The formation of graphite in the carbon component leads to an increased electrical conductivity. The graphitizing of the carbon component may here be done between 1400 and 3000° C., in one embodiment between 2300 and 2600° C.

The graphitization degree g may be calculated based on a measured distance d002 of graphite basal levels:

$$g=(344\ pm-d002)/(344\ pm-335.4\ pm)$$

A small distance d002 value thereby relates to a high graphitization degree. The particle size distribution d002 may be measured by laser diffraction and for example, based on ISO 13320-1:2009, Particle size analysis—Laser diffraction methods—Part 1: General principles.

In an example, the amount of the carbon component in the elastomer component is near a percolation threshold. Near in the meaning of within the area of the percolation threshold, only few conductive paths exist in the piezoresistive material when not subjected to a load. However, if a load is applied to the piezoresistive material, the elastomer component is compressed and the electrically conductive carbon particles get in contact with each other. Further conductive paths appear, which thus increase the electrical conductivity of the piezoresistive material. As a result, the sensitivity for pressure is extremely high near the percolation threshold. Outside the area of the percolation threshold, there is no sudden change of the electrical conductivity of the piezoresistive material.

In an example, the amount of the carbon component in the elastomer component is between 1 to 30 wt.-%, in one embodiment between 15 and 26 wt. %. In an example, the carbon particles have a particle size distribution d50 between 1 and 100 μm, in one embodiment between 5 and 20 μm. The particle size distribution d50 may be measured by laser diffraction and for example, based on ISO 13320-1:2009, Particle size analysis—Laser diffraction methods—Part 1: General principles.

In an example, only pores larger than a filling threshold are infiltrated by polymeric chains. Exemplarily, the filling threshold is between 60 and 250 nm, and in one embodiment between 60 and 150 nm. The filling threshold may be measured by Scanning Electron Microscopy (SEM) and for example by means of the scanning electron microscope "FEI Nova NanoSEM 450". The dimensions (length and/or diameter) of the pores not filled with the elastomer component may be determined on basis of a digital scale of the scanning electron microscope.

In an example, the carbon component has a real density between 1.6 and 2.26 g/cm$^3$, and in one embodiment between 2.0 and 2.26 g/cm$^3$. The density may be measured by He pycnometry and for example, based on the DIN 66137-2 (December 2004) standard.

In an example, the carbon component has a specific surface between 5 and 500 m$^2$/g, and in one embodiment between 10 and 70 m$^2$/g. The specific surface may be measured by physical gas adsorption according to BET (Brunauer-Emmett-Teller) and for example, based on DIN ISO 9277:1995.

In an example, the elastomer component includes rubber and/or silicone. Rubber may be styrene butadiene rubber, ethylene propylene diene monomer rubber or the like. The silicone of the elastomer component may have a viscosity in an uncured state between 10 Pa s and 2000 Pa s when measured for example, according to DIN53019.

The catheter system according to one embodiment can be used for sensing, ablation, stimulation, delivery and/or insertion. It can therefore be used in or as a pig tail catheter device, a balloon catheter device, a renal ablation device, a delivery catheter, a cochlea implant, a cardiac resynchronization device, a pacemaker, a neuro stimulation device, a fluid pressure monitoring device, and/or a stent. The catheter system may avoid harming or unintentionally penetrating surrounding medium or tissue when moving a catheter for example, through blood vessels, in a cochlea or within the heart to assist to a navigation of the catheter through the surrounding medium. It may also provide an inflation feedback for a balloon of a balloon catheter device, a renal ablation device or a drug delivery device to, for example, enable an automated inflation or deflation including feedback. The catheter system when being part of an ablation process may further allow a better control of the ablation parameters.

The catheter system according to one embodiment can be used as a probe to detect a force, pressure, motion and/or vibration of the probe relative to a surrounding medium. The force may be in a range of 0.02 N to 10 N. Further, a detection of a change in force, pressure, motion, vibration etc. is possible. In addition, a detection of acceleration or elongation or their changes is possible. The surrounding medium may be gaseous, liquid or solid. It may be bone, tissue, organs, blood and/or the like. When using several probes, also a detection of a position of an occurrence or a change in force, pressure, motion, vibration etc. is possible.

According to one embodiment, also a method for manufacturing a catheter system is presented. It includes the following steps:
a) providing an at least partially flexible catheter body,
b) providing at least a strain gauge, and
c) providing at least a ring electrode to surround at least a portion of the flexible catheter body.

The strain gauge and the ring electrode are allocated to each other. The strain gauge is configured to measure a deformation of the flexible catheter body at a position allocated to the ring electrode to detect a contact between the ring electrode and tissue.

For example, the manufacturing method of a catheter system with at least two ring electrodes may include
a provision of a flexible tube with a longitudinal opening out of a plastic material and for example, out of a thermoplastic elastomer as a catheter body,
an insertion of at least two distant holes into a wall of the tube,
a provision of at least two wires out of a metallic material and for example, out of a Nickel-Cobalt base alloy to enter the tube through the longitudinal opening and to exit the tube through one of the holes, respectively,
a fixing of at least two rings out of a metallic material and for example, out of a platinum-iridium alloy as ring electrodes to the at least two wires, and
a fixing of the rings around the tube at the positions of the holes.

The manufacturing method of a catheter system may further include
an at least partially coating of above assembly, and
an application of a deformation sensitive material as strain gauges on the rings by means of for example, printing and optionally curing.

It shall be understood that the catheter system, the use of such catheter system and the manufacturing method for such catheter system according to the independent claims have similar and/or identical embodiments, for example, as defined in the dependent claims. It shall be understood further that embodiments can also be any combination of the dependent claims with the respective independent claim.

FIG. 1 illustrates schematically and exemplarily an embodiment of a catheter system 10 according to one embodiment. The catheter system 10 includes a flexible catheter body 11, several ring electrodes 12 and several strain gauges 13. The ring electrodes 12 surround portions of the flexible catheter body 11.

The strain gauges 13 are allocated or assigned to the ring electrode 12 and are configured to measure a deformation of the flexible catheter body 11 at a position allocated to the ring electrode 12 to detect a contact between the ring electrode 12 and tissue. The strain gauges 13 have here an electrical connection to the respective one of the ring electrodes 12 and are arranged in the proximity of the respective one of the ring electrodes 12.

The use of a flexible catheter body 11 allows a movement of the catheter system 10 in a human body and a measurement of the catheter body 11's deformation at each position of the strain gauges 13 and thereby at each position of the ring electrodes 12. The measured deformation or deflection is then used to detect a contact between the strain gauge 13 and thereby the ring electrode 12 and surrounding tissue and to calculate a contact force of the strain gauge 13 and thereby the ring electrode 12. In detail:

The strain gauges 13 output a change of electrical resistance depending on the deformation of the catheter body 11 at the position allocated to the respective ring electrode 12. The catheter system 10 or a processing unit calculates a contact force between the respective ring electrode 12 and tissue based on the respective change of electrical resistance. Thereto, an electrical resistance detected by the strain gauge 13 is calculated into a value of compressive load applied to the ring electrode 12 and the strain gauge 13. For example, a decrease of electrical resistance detected by the strain gauge 13 is processed into a value of compressive load applied to the catheter system 10 strain gauge 13 and the ring electrode 12.

Figure 2:
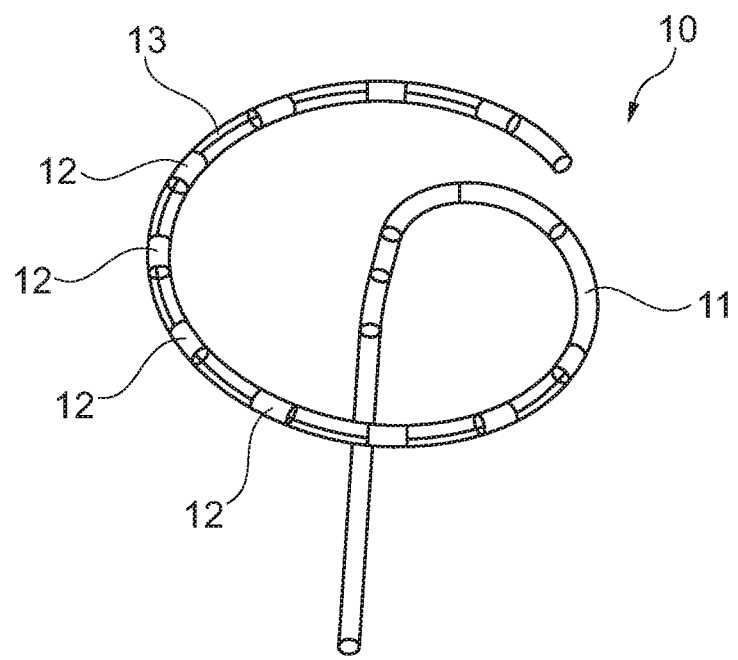
FIG. 2 illustrates schematically and exemplarily a further embodiment of a catheter system according to one embodiment.
Figure 3:
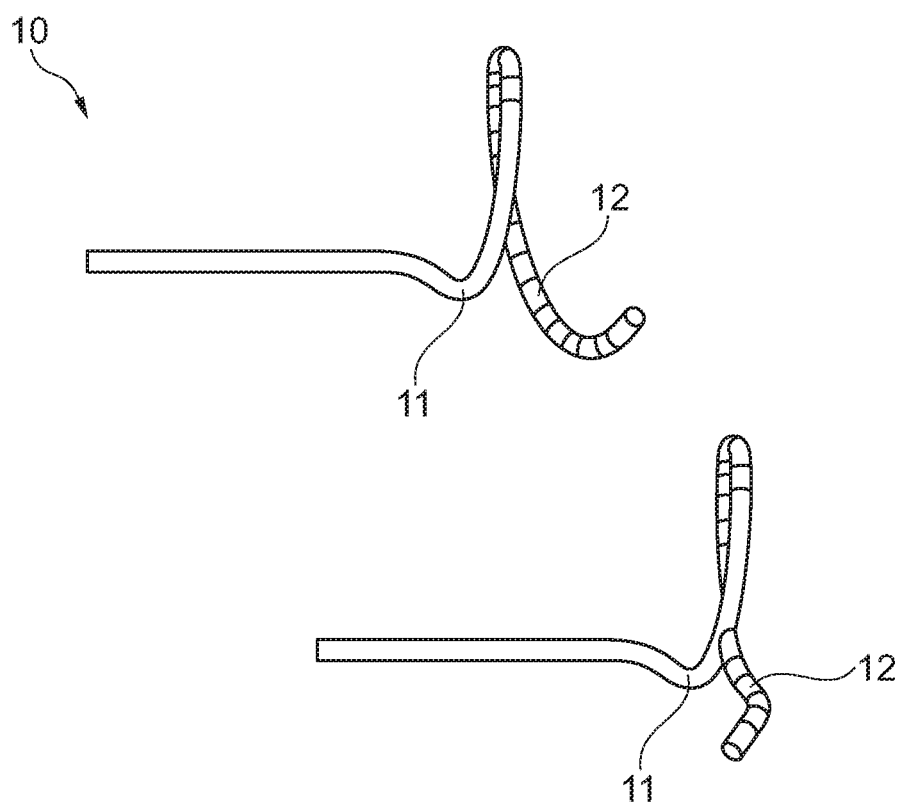
FIG. 3 illustrates schematically and exemplarily a further embodiment of a catheter system according to one embodiment.

FIGS. 2 and 3 illustrate schematically and exemplarily a further embodiment of a catheter system 10 according to one embodiment. The catheter body 11 is here a Pig Tail catheter, which has a helical shape to surround an area of tissue for, for example, pulmonary vein ablation. The catheter system 10 again includes several strain gauges 13 and several ring electrodes 12 distributed along the catheter body 11 with distances between each other. The strain gauges 13 have a strain gauge body with a tubular shape extending inside the catheter body 11. The strain gauges 13 are again allocated to one of the ring electrodes 12 and measure a deformation of the flexible catheter body 11 at the respective positions allocated to ring electrodes 12 to detect a contact between the respective electrode and the tissue.

Figure 4A:
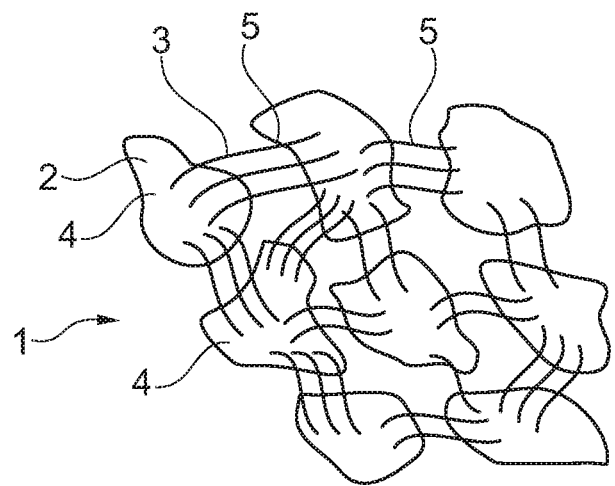
FIGS. 4a-4c illustrate schematically and exemplarily an embodiment of the piezoresistive material according to one embodiment.
Figure 4B:
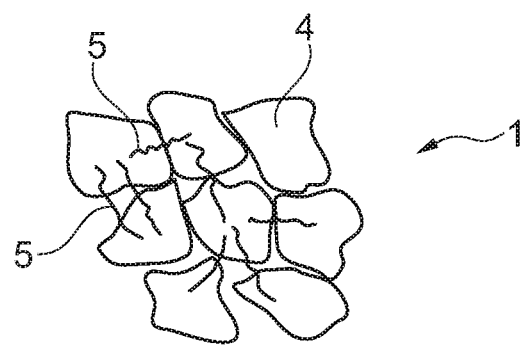
Figure 4C:
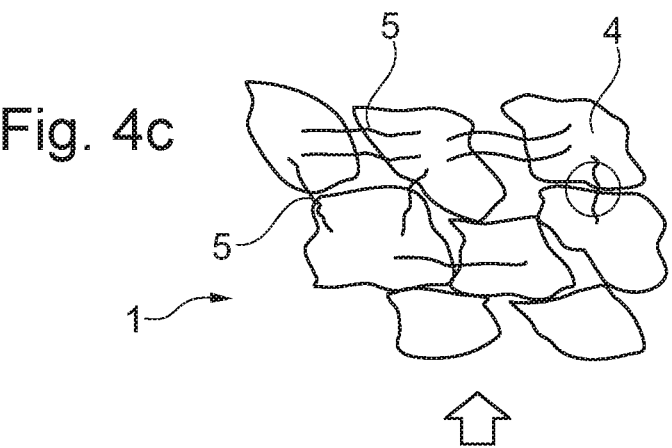

The strain gauge 13 is made of a piezoresistive material 1 including a carbon component and an elastomer component. FIGS. 4a-4d illustrate schematically and exemplarily an embodiment of the piezoresistive material 1 according to one embodiment. FIG. 4a illustrates the piezoresistive material 1 with no load or pressure. FIG. 4b illustrates the piezoresistive material 1 with isostatic load or pressure. FIG. 4c illustrates the piezoresistive material 1 with uniaxial load or pressure.

As illustrated in FIG. 4a, the piezoresistive material 1 includes a compound of a carbon component 4 and an elastomer component 3. The carbon component 2 includes porous carbon particles 4, which include macropores (not illustrated). The elastomer component 3 includes pre-stressed polymeric chains 5. Most of the macropores in the carbon particles 4 are infiltrated by polymeric chains 5. Further, most carbon particles 4 are linked by polymeric chains 5.

As illustrated in FIGS. 4b and 4c, the piezoresistivity of the piezoresistive material 1 is based on the fact that the polymeric chains 5 between the carbon particles 4 of the carbon component 2 rearrange and relax when the piezoresistive material 1 is subjected to a compressive load (isostatic in FIG. 4b, uniaxial in FIG. 4c). The rearrangement and relaxation enables a formation of electrical paths between the carbon particles 4 and consequently reduces the electrical resistance of the piezoresistive material 1.

The elastomer component 3 is here a silicone precursor.

Figure 5:
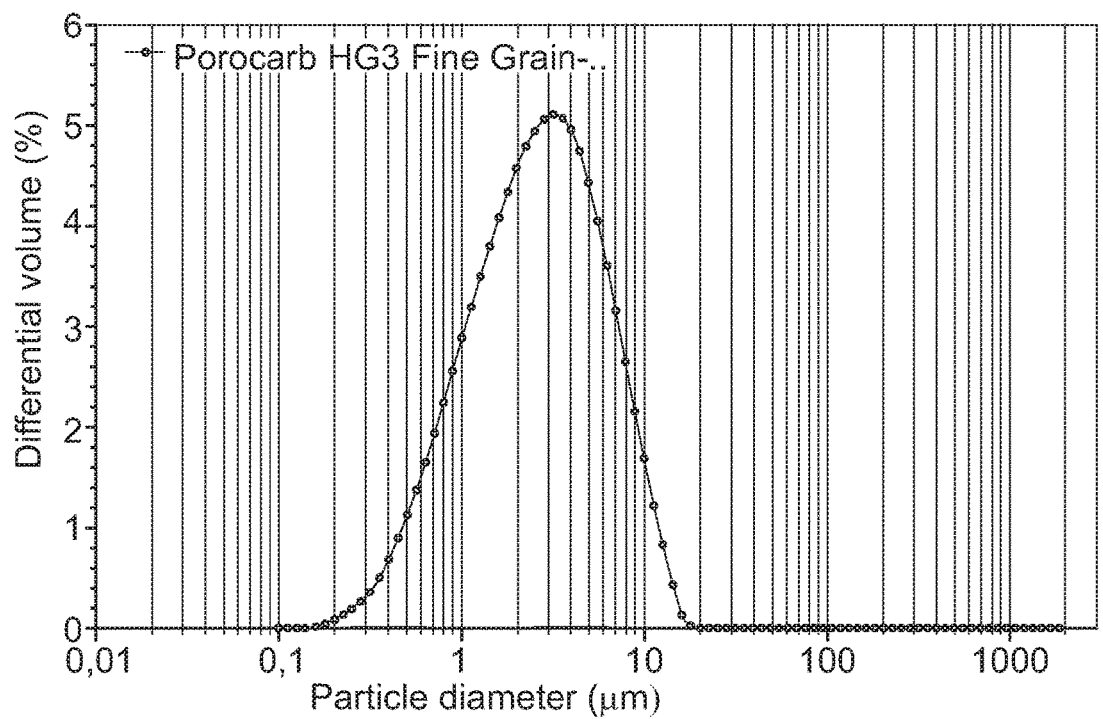
FIG. 5 illustrates a particle size distribution for an exemplary carbon component.
Figure 6:
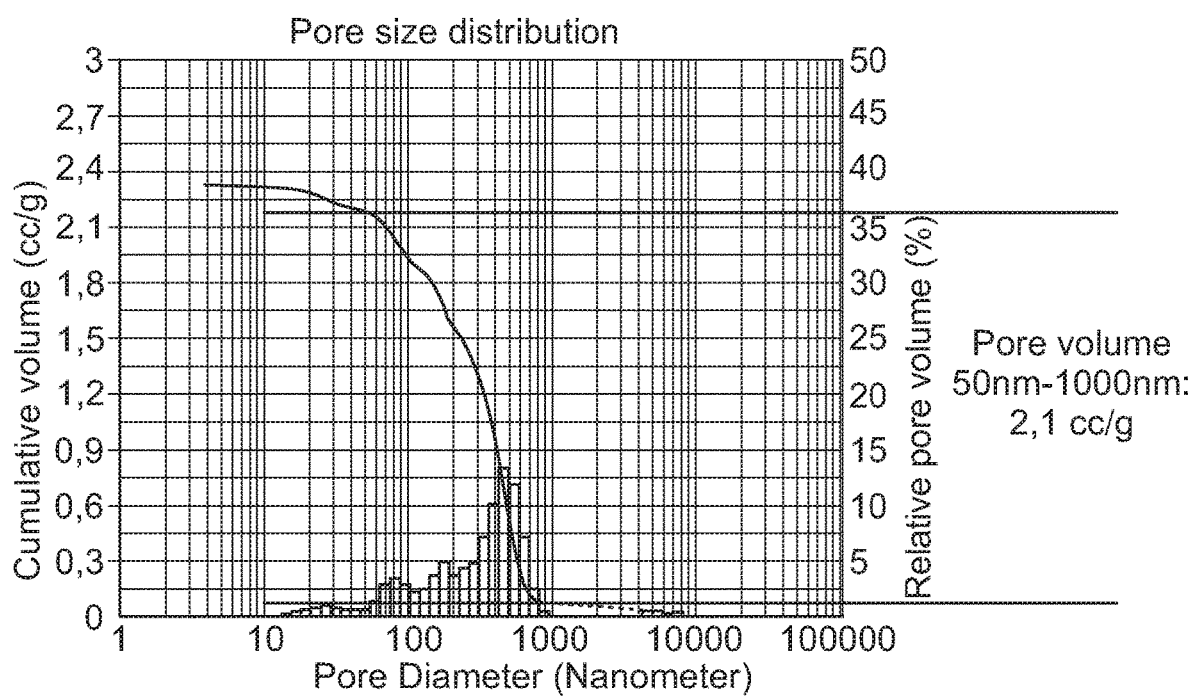
FIG. 6 illustrates a pore size distribution for an exemplary carbon particle.

The carbon component 2 includes highly porous carbon particles 4 with open porosity. The pores of the carbon particles 4 include macropores with a size between 50 and 1000 nm. FIG. 5 illustrates a particle size distribution for an exemplary carbon component 2. The carbon particles 4 of the carbon component 2 are mainly between 1 and 20 μm. FIG. 6 illustrates a pore size distribution for an exemplary carbon particle 4. The total pore volume of the macropores is here 2.1 cm³/g and lies in general between 0.7 and 2.5 cm³/g. The carbon particles 4 further include mesopores with a size between 2 and 50 nm.

Here, only pores larger than a filling threshold between 60 and 250 nm are infiltrated by polymeric chains 5. Small macropores and mesopores are not filled. Micropores essentially do not exist due to a graphitization of the material.

The amount of the carbon component 2 in the material is near a percolation threshold P, which is here 18 wt.-%.

Figure 7:
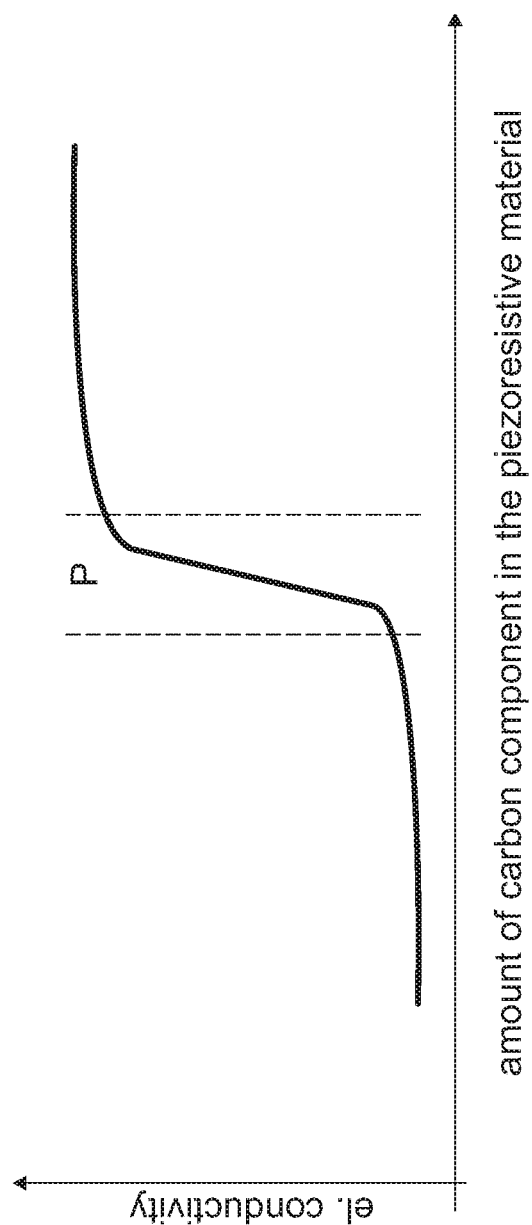
FIG. 7 illustrates a schematic overview of an electrical conductivity of a piezoresistive material depending on a carbon concentration.

FIG. 7 illustrates a schematic overview of an electrical conductivity of the piezoresistive material 1 depending on a carbon concentration without external load. The curve illustrates within the area of the percolation threshold P a change of the electrical conductivity of the material. Below and above the area of the percolation threshold P, there is no sudden change of the electrical conductivity of the material.

When subjected to a load, the elastomer component 3 is compressed and thereby no longer blocks a contact between the actually electrically conductive carbon particles 4. Electrically conductive paths appear between the carbon particles 4. As the amount of the carbon component 2 in the piezoresistive material 1 is near the percolation threshold P, the appearance of the conductive paths leads to a sudden increase of the electrical conductivity of the piezoresistive material 1. The sudden increase of the electrical conductivity can be easily detected. As a result, near the percolation threshold P, the sensitivity for pressure is extremely high. Outside the area of the percolation threshold P, there is no sudden change of the electrical conductivity of the piezoresistive material 1.

Figure 8:
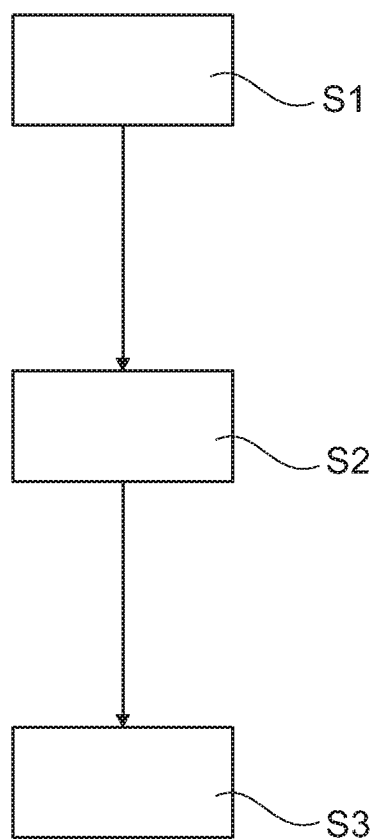
FIG. 8 illustrates basic steps of an example of a method for producing a piezoresistive material according to one embodiment.

FIG. 8 illustrates a schematic overview of steps of a manufacturing method for a catheter system 10 according to one embodiment. The method includes the following steps:

In a first step S1, providing an at least partially flexible catheter body 11.

In a second step S2, providing at least a strain gauge 13.

In a third step S3, providing at least a ring electrode 12 to surround at least a portion of the flexible catheter body 11.

The strain gauge 13 and the ring electrode 12 are allocated to each other and the strain gauge 13 is configured to measure a deformation of the flexible catheter body 11 at a position allocated to the ring electrode 12 to detect a contact between the ring electrode 12 and tissue.

Examples

As elastomer component, the two-component silicon Elastosil LR 3003/10 (Wacker Chemie AG) is used. Both subcomponents of Elastosil LR 3003/10 are liquid and highly viscous (η=74.000 mPa*s).

As carbon component, the macroporous carbon Porocarb® HG3 Fine Grain (Heraeus) is used. Porocarb HG3 Fine Grain has a specific surface of 57 m²/g and a particle size d50 of 4 μm.

The carbon component is dispersed in both subcomponents of the elastomer component separately. This is done by means of a roller mill. Both subcomponents filled by the carbon component are then mixed with a 1:1 ratio to obtain the piezoresistive material.

The piezoresistive material is formed into a plate- and a rod-shape and cured in an oven for 4 hours at 200° C.

Figure 9:
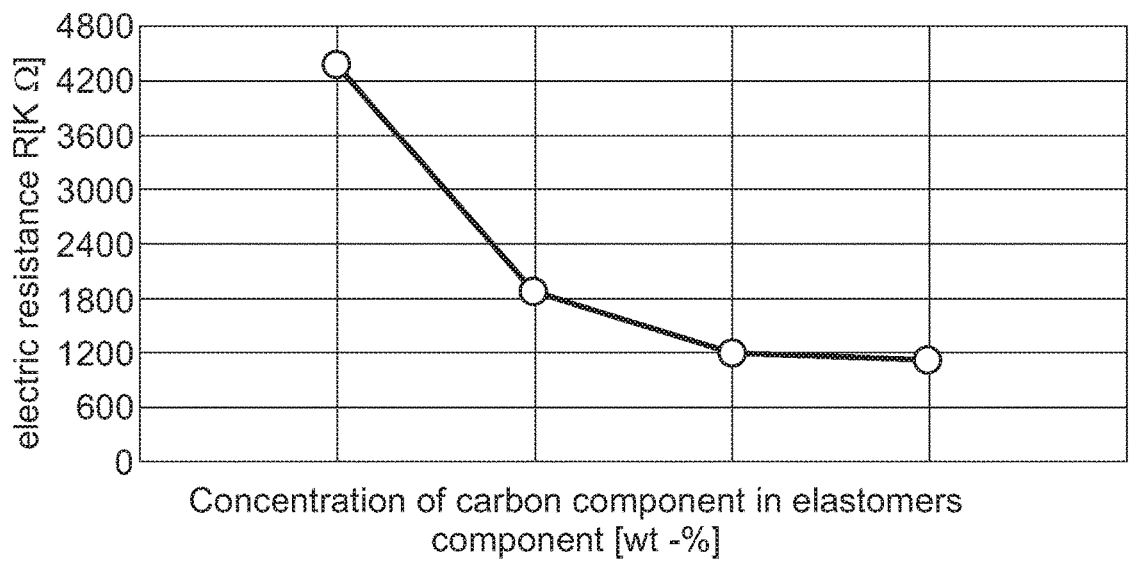
FIG. 9 illustrates a percolation threshold.

To detect a percolation threshold, several samples of the piezoresistive material with different concentrations of carbon particles are made and their electric conductivity is measured without any external force/pressure. The result is illustrated in FIG. 9. The electric conductivity is detected starting at a carbon particle concentration of 18 wt.-%. A maximum change of electric resistance (2503 kΩ) is detected for a carbon particle concentration between 18 wt.-% and 19 wt.-%. Starting at a carbon particle concentration of 21 wt.-%, no considerable change of the electric resistance is detected.

The samples of the piezoresistive material are subjected to unidirectional and isostatic pressure tests. Unidirectional pressure tests are made by means of a compression die. Isostatic pressure tests are made by means of a pressure chamber. The electric resistance is monitored by a multimeter (for example, Agilent 34401a).

Figure 10:
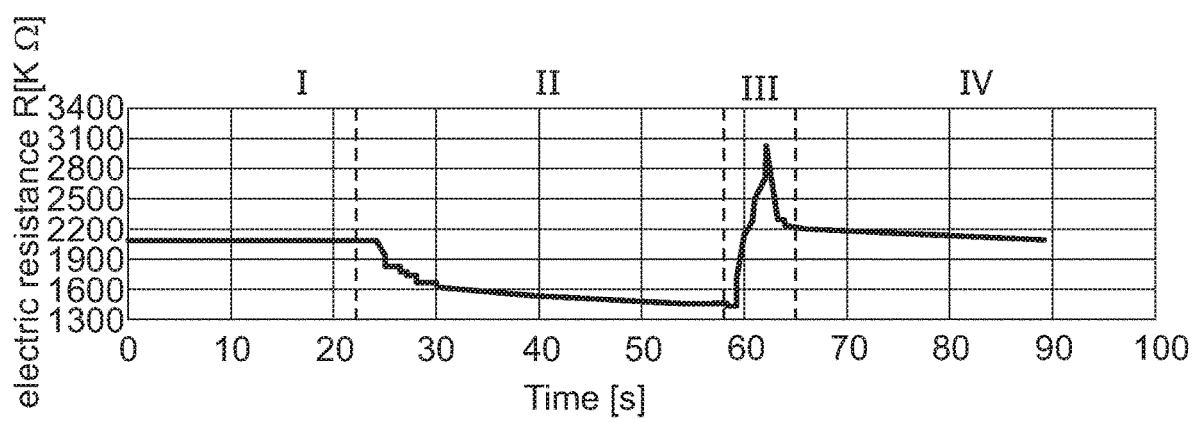
FIG. 10 illustrates the detected electric resistance for an increasing load.

FIG. 10 illustrates the detected electric resistance for an increasing load. Area I illustrates the electric resistance before the application of a load. In area II, the application of a load starts and the electric resistance decreases. The negative change of electric resistance for a load between 0 and 4 N amounts to 614 kΩ. Area III illustrates a peak when unloading the sample and a decrease of the electric resistance after unloading the sample. Area IV illustrates the return of the electric resistance to its initial value.

Figure 11:
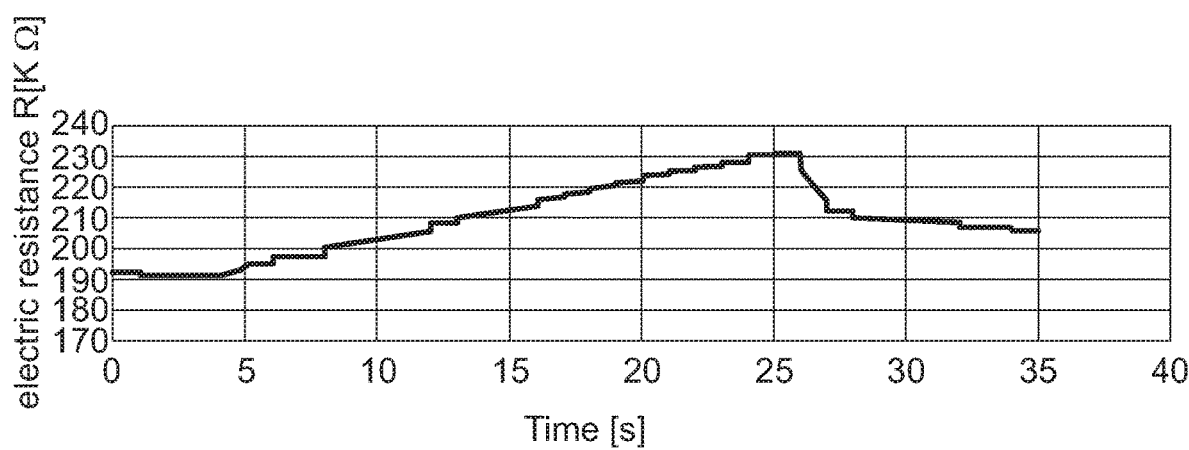
FIG. 11 illustrates a detected electric resistance for a linear increase of blood pressure.

FIG. 11 illustrates a detected electric resistance for a sudden increase of blood pressure. The sudden increase of blood pressure leads to a considerable change of the detected electric resistance of the piezoresistive material, which thereby illustrates a great sensitivity for pressure changes.

As elastomer component, also the latex emulsion dispersion Lanxess S-62F can be used. Lanxess S-62F includes 68 wt.-% of styrene butadiene rubber and has a nominal density of 0.94 g/cm$^3$. As carbon component, the carbon modification Porocarb HG3 Fine Grain (Heraeus) can be used again.

In a further example, 210 gr Porocarb HG-3FG are added to 1162 gr Lanxess S-62F to obtain a carbon concentration of 21 wt.-%, The mixture is agitated for 15 min. During further agitation, 70 gr diluted sulfuric acid (pH 3) with 1.4 gr of a polymere quaternary amine (for example, Perchem 503) are added at 60° C. SBR latex particles coagulate and precipitate. The liquid phase is separated by centrifugation.

As a result, an SBR rubber compound material is obtained. It is further agitated by a Brabender mixer B50 up to a temperature of 100° C. and cooled to 50° C. 2.5 gr Dicumyl peroxide (Sigma-Aldrich) are added to initiate cross-linking. The mixture is again agitated at 60° C. in the Brabender mixer, removed from the mixer and formed to samples to be tested as described above.

FIGS. 12a-12d illustrate data of four static pressure tests conducted with Porocarb material to be used as carbon component in the piezoresistive material of the strain gauge according to one embodiment.

Figure 12A:
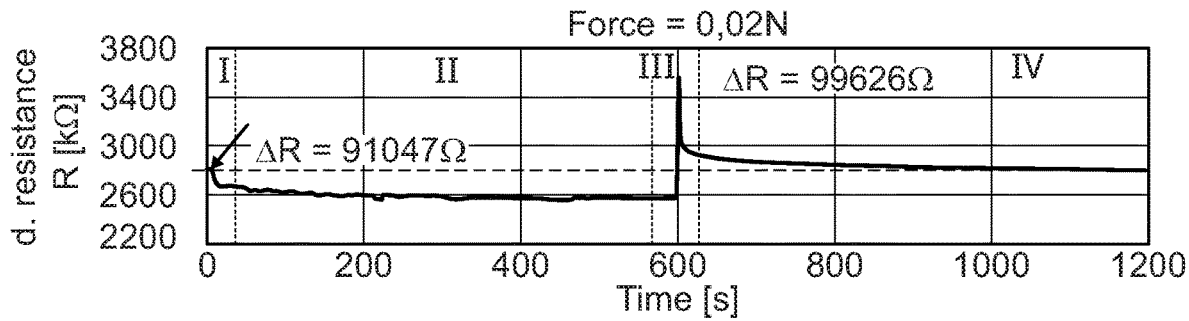
FIG. 12a-12d illustrate data of four static pressure tests conducted with Porocarb®.
Figure 12B:
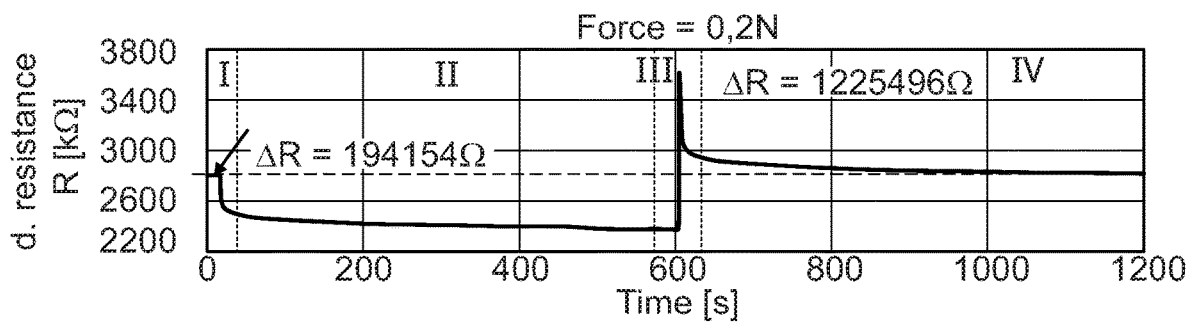
Figure 12C:
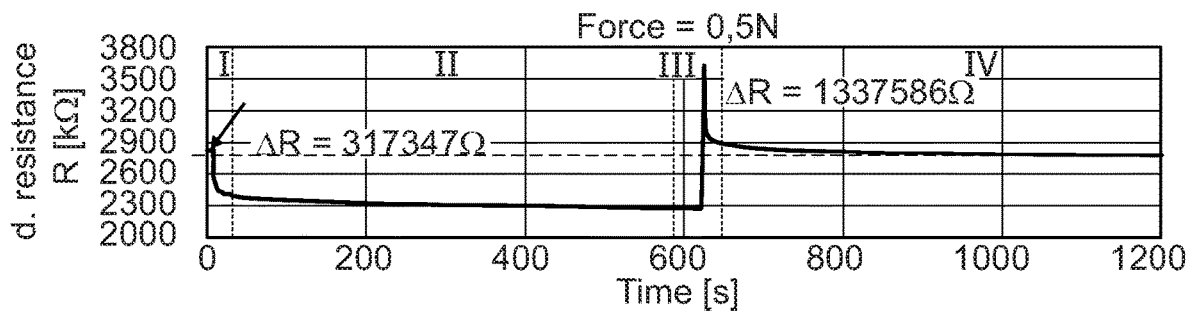
Figure 12D:
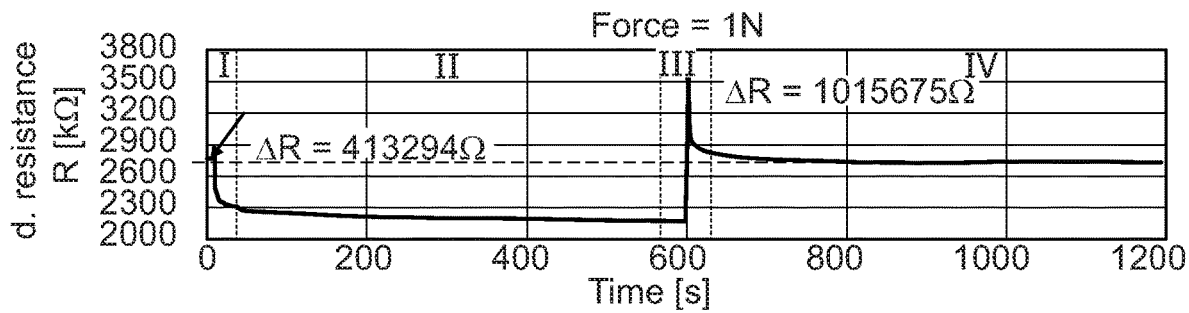

Porocarb is subjected to forces of 0.02 N (FIG. 12a), 0.2 N (FIG. 12b), 0.5 N (FIG. 12c) and 1 N (FIG. 12d). The material includes between 18 and 21 wt. % porocarb particles in silicone. The arrow indicate a starting point before the sample is subjected to the respective force. In zone I, the respective force is applied, in zone II, the force is held constant, in zone III, the force is removed, and in zone IV, the sampled is relaxed. As indicated by dotted lines, in zone III, the material relaxes back to its original state as it was before the application for the force. The electrical resistance decreases in zones I and II. In zone III, it rapidly increases above an initial resistance value and rapidly decreases again within seconds to a value close to the initial resistance value. In zone IV, the electrical resistance further slightly decreases.

As a result, Porocarb used as carbon component in the piezoresistive material of the strain gauge according to one embodiment and as defined in the claims may provide the benefit to be elastic enough to not limit a flexibility of the catheter system and to give a very sensitive feedback of a change of electrical resistance.

Figure 13A:
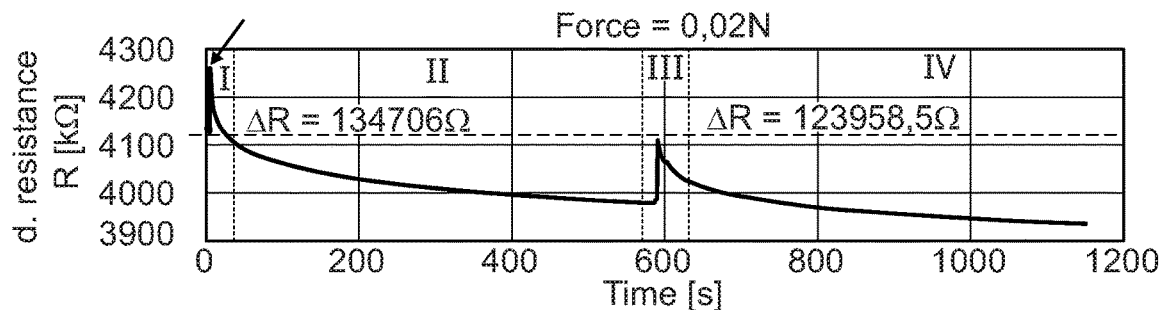
FIG. 13a-13d illustrates data of four static pressure tests conducted with carbon black.
Figure 13B:
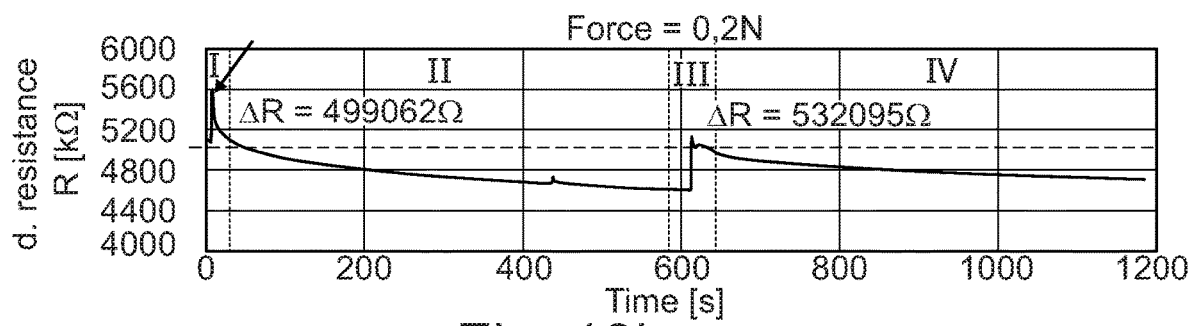
Figure 13C:
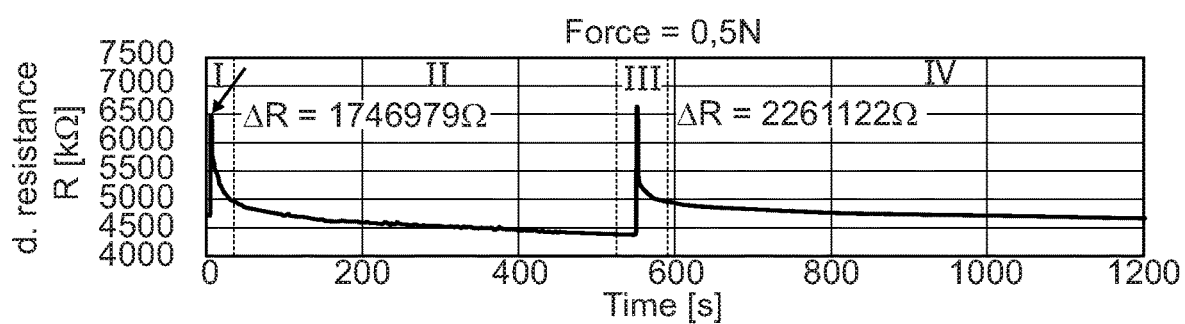
Figure 13D:
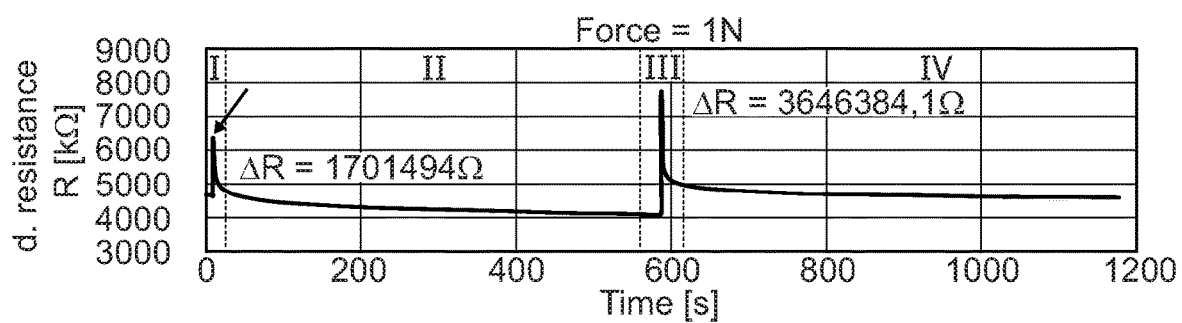

This is in contrast to other carbon materials, as for example, carbon black and carbon nanotubes. FIGS. 13a-13d thereto illustrate data of four static pressure tests conducted with carbon black subjected to forces of 0.02 N (FIG. 13a), 0.2 N (FIG. 13b), 0.5 N (FIG. 13c) and 1 N (FIG. 13d). The material includes between 25 and 28 wt. % carbon black particles in silicone. The arrow indicate a starting point before the sample is subjected to the respective force. In zone I, the respective force is applied, in zone II, the force is held constant, in zone III, the force is removed, and in zone IV, the sampled is relaxed. As indicated by dotted lines, in zone III, the material does not relax back to its original state as it was before the application for the force. The electrical resistance decreases rapidly below an initial resistance value in zone I and further decreases in zone II, but considerably slower than in zone I. In zone II, carbon black illustrates a bigger drift in the electrical signal than Porocarb (see FIG. 12). In zone III, it rapidly increases and decreases again. In zone IV, the electrical resistance further slightly decreases to a value below the initial resistance value.

Figure 14A:
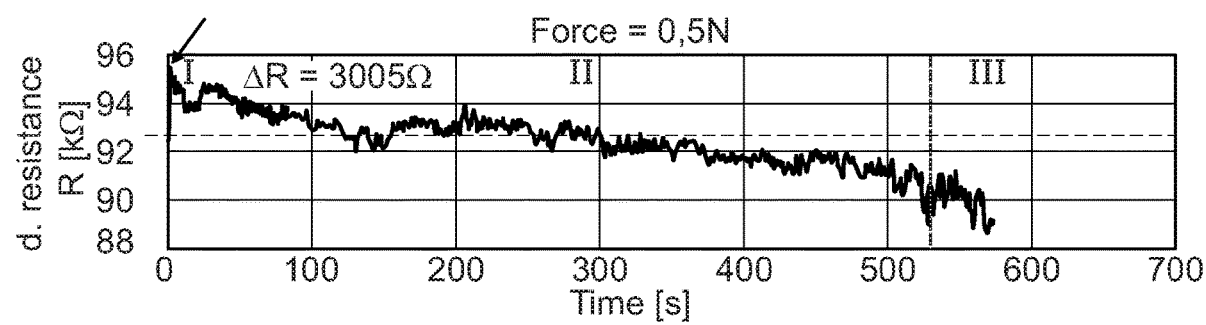
FIG. 14a-14b illustrate data of four static pressure tests conducted with carbon nanotubes.
Figure 14B:
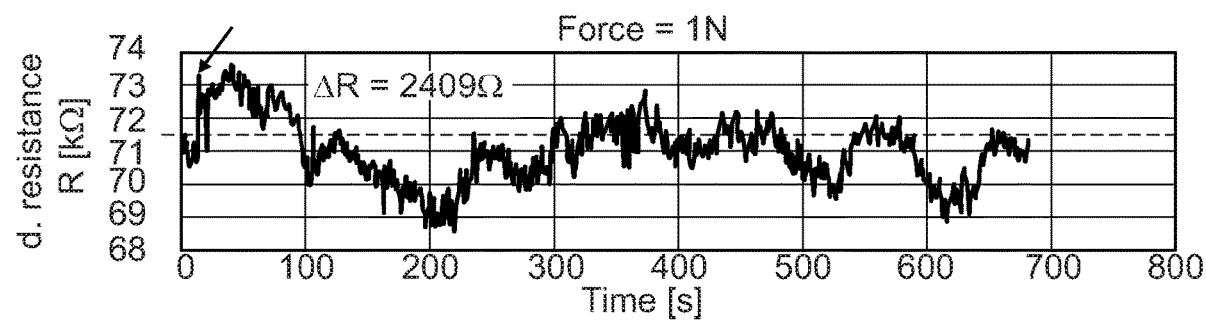

FIGS. 14a-14b illustrates data of four static pressure tests conducted with carbon nanotubes subjected to forces of 0.5 N (FIG. 14a) and 1 N (FIG. 14b). The material includes between 2 and 5 wt. % carbon nanotube particles in silicone. The arrow indicate a starting point before the sample is subjected to the respective force. In zone I, the respective force is applied, in zone II, the force is held constant, and in zone III, the force is removed. As indicated by dotted lines, in zone III, the material does not relax back to its original state as it was before the application for the force. The electrical resistance rapidly increases in zone I and then decreases in zones II and III below an initial resistance value. At a force of 1 N, there is no relaxation of the material to its original state.

A comparison of FIGS. 12a-12d to 14a-14b illustrates that a strain gauge made of a piezoresistive material including Porocarb as carbon component in an elastomer component may give the most sensitive feedback of a change of electrical resistance. Porocarb is extremely sensitive and a response to a force in form of a change of electrical resistance may be found for very small forces below for example, 0.02 N. The strain gauge including Porocarb and being part of a catheter system further allows a return to an initial state after having experienced a force, for example, a smaller or larger force between 0.02 N and 1 N.

Test Methods

If a test method is not specified for a particular parameter, the standard test method known in the art has to be applied. This shall be for example, the test method according to the corresponding DIN and/or ISO regulation, which publication date is closest to the filing date of the present application. If measurement conditions are not specified, the standard conditions according to the IUPAC standard have to be applied (SATP conditions), which are 298.15 K for temperature and 100 kPa for absolute pressure.

Pore Volume and Pore Size

The specific pore volume of a porous material is the free volume of the material which is occupied by cavities.

The pore volume and pore size of the carbon particles is determined by means of mercury porosimetry according to the ISO 15901-1 (2005) standard. According to this method, mercury as a non-wetting liquid is intruded at high pressure and against the surface tension forces of the probe into the pores of the porous material. Since the force required for intrusion is inversely proportional to the pore size, this method allows determination of the cumulative total pore volume and of the pore size distribution of the sample.

The porosimeter used was the "ThermoFisher Scientific PASCAL 140" for low pressure measurements (until 4 bar) and the "Thermo isher Scientific PASCAL 440" for high pressure measurements (until 4000 bar). Both instruments were calibrated by means of porous glass squares with a standardized pore diameter of 75 nm (obtained from Universität Leipzig, Fakultät für Chemie and Mineralogie, Institut für Technische Chemie). Using the Washburn method, the mercury density for the actual temperature was corrected. For the surface tension, a value of 0.484 N/m and for the contact angle a value of 141.1° was set. The sample size was between 30 and 40 mg. Before the start of the measurement, the test sample was dried at 120° C. for 24 h in vacuum at an absolute pressure of 0.01 kPa.

Specific Surface

The specific surface of the carbon component is determined by means of a sorption measurement according to the method of Brunauer, Emmet and Teller (BET method) according to the DIN ISO 9277:1995 standard.

The instrument used was the "Quantachrome NOVA-3000", which operates according to the SMART method (sorption with adaptive rate dosing). The reference materials used were Alumina SARM-13 and SARM-214, both provided by the manufacturer of the instrument. The saturation vapour pressure of Nitrogen ($N_2$ 4.0) was determined and the test sample dried under vacuum for 1 hour at 200° C. After cooling, the weight of the test sample was determined and subsequently degassed by evacuation to an absolute pressure of 200 mbar. In that pressure range, where monolayers and multiple layers of absorbed molecules are formed, the specific surface area (BET-SSA) was determined from the multi-adsorption isotherm (BET isotherm) according to Brunauer, Emmet and Teller.

Particle Size Distribution

The particle size and particle size distribution of the carbon particles is determined by means of laser diffraction of a dispersed sample according to ISO 13320.

The instrument used was a Mastersizer 3000 (Malvern) using a He—Ne laser, a Blue LED and a wet dispersing unit for measurements at ambient temperature (23° C.). The wet dispersing unit was adjusted to an ultrasonic output of 80%, and water served as a dispersant. The d50 values of the particle size distribution were determined using the device software 21 CFR with a form factor of 1.

The d50 value is defined as the particle size which does not reach 50% of the cumulative particle volume (Median value of the particle size).

Density

The sediment density of the carbon component is determined by gaspycnometry using a "Thermo Pycnomatic ATC" according to DIN 66137-2 (December 2004) with Helium as the sample gas.

The sample weight was 0.5±0.1 g, using a cell volume of approximately 7.5 $cm^3$, a reference volume of approximately 20 $cm^3$, an equilibrium delta time of 12 sec and a temperature of 20.0° C. at 2 bar pressure. Before measuring, the sample was dried for 1 h at 200° C. under vacuum.

Graphitization Degree

The graphite basal level distances d002 are measured by X-ray diffraction and calculated on basis of the Scherrer equation.

The graphitization degree g of the carbon particles was then calculated based on the measured distance d002 of graphite basal levels: g=(3414 pm-d002)/(344 pm-335.4 pm).

Electrical Conductivity and Percolation Threshold

To determine the percolation threshold of the piezoresistive material, dispersion samples with different concentrations of the carbon component were produced. For each carbon particle concentration four strand-like probes of pressed material were manufactured from the dispersion. To determine the percolation threshold, the electrical conductivity of the probe was determined according to the following method.

An electrical current was applied to the probe by means of electrodes with gold-plated surfaces and the voltage drop of the probe was measured. Based on the measured value and the applied current, the electrical resistance and hence the electrical conductivity of the probe (in S/cm) was determined. A measured value of more than 1 S/cm was evaluated as being "electrically conductive".

After a carbon particle concentration resulting in an electrical conductivity was found, further dispersions with similar particle concentrations were produced and the electrical conductivity was determined accordingly.

Filling Threshold

The filling threshold of the carbon particles was determined by Scanning Electron Microscopy (SEM) with the Scanning electron microscope "FEI Nova NanoSEM 450".

The dimensions (length and/or diameter) of the pores not filled with the elastomer component were determined on basis of the digital scale of the Scanning electron microscope.

It has to be noted that embodiments are described with reference to different subject matters. For example, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While embodiments are illustrated and described in detail in the drawings and foregoing description, such illustration and description are to be considered illustrative or exemplary and not restrictive. Embodiments are not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A catheter system comprising:
 a catheter body, wherein at least a part of the catheter body is flexible;
 at least one ring electrode; and
 at least one strain gauge;
 wherein the at least one ring electrode surrounds at least a portion of the flexible part of the catheter body;
 wherein the at least one strain gauge is arranged in a proximity of the at least one ring electrode;

wherein the at least one strain gauge is configured to measure a deformation of the flexible part of the catheter body at a position in a proximity of the at least one ring electrode to indirectly detect a contact between the at least one ring electrode and tissue;

wherein the at least one strain gauge comprises a piezoresistive material comprising a carbon component and an elastomer component;

wherein the carbon component comprises carbon particles comprising macropores having a pore size between 50 nm and 1,000 nm measured by Hg porosimetry; and wherein the piezoresistive material has an original state and the carbon particles allow the piezoresistive material to relax back to the original state when a force is removed.

2. The catheter system according to claim 1, wherein the catheter system is a pig tail catheter.

3. The catheter system according to claim 1, wherein the at least one strain gauge has a tubular shape and extends at least partially inside the catheter body.

4. The catheter system according to claim 1, wherein the at least one ring electrode and the at least one strain gauge are arranged at a distal tip of the catheter body.

5. The catheter system according to claim 1, wherein the at least one strain gauge is configured to output a change of electrical resistance depending on the deformation of the flexible part of the catheter body at the position and proximity of the at least one ring electrode, and wherein the catheter system further comprises a processing unit configured to calculate a contact force between the at least one ring electrode and tissue based on the change of electrical resistance.

6. The catheter system according to claim 5, wherein the processing unit is spaced apart from the at least one ring electrode.

7. The catheter system according to claim 1 wherein the elastomer component comprises polymeric chains, and wherein at least some of the macropores in the carbon particles are infiltrated by polymeric chains to form a piezoresistive interconnection between the carbon particles.

8. The catheter system according to claim 7, wherein the polymeric chains are configured to rearrange when the piezoresistive material is subjected to the force so that electrical paths form between the carbon particles to decrease an electrical resistance of the piezoresistive material.

9. The catheter system according to claim 1, wherein the carbon particles are highly porous with a total pore volume between 0.7 and 3.5 cm$^3$/g measured by Hg porosimetry.

10. The catheter system according to claim 1, wherein the macropores in the carbon particles have a macropore volume between 0.6 and 2.4 cm$^3$/g measured by Hg porosimetry.

11. The catheter system according to claim 1, wherein the carbon particles further comprise mesopores with a pore size between 2 and 50 nm and a mesopore volume between 0.05 and 0.2 cm$^3$/g measured by Hg porosimetry.

12. The catheter system according to claim 1, wherein the carbon component is graphitized to a graphitization degree between 60 and 80%.

13. The catheter system according to claim 1, wherein the carbon particles comprise no micropores with a pore size smaller than 2 nm measured based on the Brunauer-Emmet-Teller method.

14. The catheter system according to claim 1, further configured for one or more of sensing force, ablation of tissue, stimulation of tissue, delivery of a drug and insertion of an implant.

15. The catheter system according to claim 1, further configured in a pig tail catheter device, a balloon catheter device, a renal ablation device, a delivery catheter, a cochlea implant, a cardiac resynchronization device, a pacemaker, a neuro stimulation device, a fluid pressure monitoring device, and/or a stent.

16. The catheter system according to claim 1, wherein the catheter body forms a helical shape configured to surround an area of tissue, wherein the catheter system comprises at least a first and a second strain gauge and at least a first and a second ring electrode, wherein the first strain gauge is arranged in proximity of the first ring electrode and the second strain gauge is arranged in proximity of the second ring electrode, wherein the first strain gauge is configured to measure the deformation of the flexible part of the catheter body at a position and in proximity of the first ring electrode to indirectly detect a contact between the first ring electrode and the tissue, and wherein the second ring electrode is configured to measure the deformation of the flexible part of the catheter body at a position and in proximity of the second ring electrode to indirectly detect contact between the second ring electrode and the tissue.

17. The catheter system according to claim 1, comprising several strain gauges and several ring electrodes.

18. The catheter system according to claim 1, wherein the carbon particles have a particle size distribution d50 between 1 μm 100 μm, as measured by laser diffraction.

19. The catheter system according to claim 1, wherein the force is a force between 0.02 N and 1 N.

\* \* \* \* \*

UNITED STATES PATENT AND TRADEMARK OFFICE
CERTIFICATE OF CORRECTION

PATENT NO. : 11,590,317 B2
APPLICATION NO. : 16/151843
DATED : February 28, 2023
INVENTOR(S) : Schibli et al.

It is certified that error appears in the above-identified patent and that said Letters Patent is hereby corrected as shown below:

In the Specification

Column 13, Line 53, delete "g= (3414 pm-d002)" and insert in place thereof -- g= (344 pm-d002) --.

In the Claims

Column 16, Line 45, delete "between 1 μm 100 μm" and insert in place thereof -- between 1 μm and 100 μm --.

Signed and Sealed this
Twenty-fifth Day of April, 2023

Katherine Kelly Vidal
*Director of the United States Patent and Trademark Office*